(12) United States Patent
Hadba

(10) Patent No.: US 8,007,822 B2
(45) Date of Patent: Aug. 30, 2011

(54) BIOABSORBABLE COMPOSITION AND COATINGS INCLUDING SAME

(75) Inventor: Ahmad R. Hadba, Wallingford, CT (US)

(73) Assignee: Tyco Healthcare Group LP, North Haven, CT (US)

( * ) Notice: Subject to any disclaimer, the term of this patent is extended or adjusted under 35 U.S.C. 154(b) by 1610 days.

(21) Appl. No.: 10/543,200

(22) PCT Filed: Jan. 23, 2004

(86) PCT No.: PCT/US2004/001759
§ 371 (c)(1),
(2), (4) Date: Feb. 3, 2006

(87) PCT Pub. No.: WO2004/066927
PCT Pub. Date: Aug. 12, 2004

(65) Prior Publication Data
US 2006/0188545 A1    Aug. 24, 2006

Related U.S. Application Data

(60) Provisional application No. 60/442,730, filed on Jan. 24, 2003.

(51) Int. Cl.
*A61F 2/02* (2006.01)
(52) U.S. Cl. .................................................. 424/426
(58) Field of Classification Search .................. None
See application file for complete search history.

(56) References Cited

U.S. PATENT DOCUMENTS

| | | |
|---|---|---|
| 4,027,676 A | 6/1977 | Mattei |
| 4,043,344 A | 8/1977 | Landi et al. |
| 4,047,533 A | 9/1977 | Perciaccante et al. |
| 4,080,969 A | 3/1978 | Casey et al. |
| 4,185,637 A | 1/1980 | Mattei |
| 4,190,720 A | 2/1980 | Shalaby |
| 4,201,216 A | 5/1980 | Mattei |
| 4,582,052 A | 4/1986 | Dunn et al. |
| 4,605,730 A | 8/1986 | Shalaby et al. |
| 4,624,256 A | 11/1986 | Messier et al. |
| 4,700,704 A | 10/1987 | Jamiolkowski et al. |
| 4,705,820 A | 11/1987 | Wang et al. |
| 4,711,241 A | 12/1987 | Lehmann |
| 4,788,979 A | 12/1988 | Jarrett et al. |
| 4,791,929 A | 12/1988 | Jarrett et al. |
| 4,994,074 A | 2/1991 | Bezwada et al. |
| 5,019,096 A | 5/1991 | Fox, Jr. et al. |
| 5,032,638 A | 7/1991 | Wang et al. |
| 5,047,048 A | 9/1991 | Bezwada et al. |
| 5,100,433 A | 3/1992 | Bezwada et al. |
| 5,104,398 A | 4/1992 | Planck et al. |
| 5,123,912 A | 6/1992 | Kaplan et al. |
| 5,133,739 A | 7/1992 | Bezwada et al. |
| 5,304,205 A | 4/1994 | Shinoda et al. |
| 5,312,437 A | 5/1994 | Hermes et al. |
| 5,352,515 A | 10/1994 | Jarrett et al. |
| 5,425,949 A | 6/1995 | Bennett et al. |
| 5,641,502 A * | 6/1997 | Skalla et al. .................. 424/426 |
| 5,716,376 A | 2/1998 | Roby et al. |
| 5,817,129 A | 10/1998 | Labrecque et al. |
| 6,017,553 A | 1/2000 | Burrell et al. |
| 6,177,094 B1 * | 1/2001 | Jiang .............................. 424/426 |
| 6,183,499 B1 | 2/2001 | Fischer et al. |
| 6,267,782 B1 | 7/2001 | Ogle et al. |
| 6,878,757 B2 | 4/2005 | Roby |
| 2004/0153125 A1 | 8/2004 | Roby |

FOREIGN PATENT DOCUMENTS

| | | |
|---|---|---|
| EP | 0 436 308 | 7/1991 |
| EP | 0 501 679 | 9/1992 |
| EP | 1669093 B1 * | 2/2010 |

OTHER PUBLICATIONS

International Search Report from PCT/US04/01759.
European Search Report.

* cited by examiner

*Primary Examiner* — Carlos Azpuru

(57) ABSTRACT

Bioabsorbable compositions of A) blends of bioabsorbable homopolymers and/or copolymers containing glycolide and lactide and B) salts of fatty acids and/or fatty acid esters are described. Processes for making the compositions and surgical articles made totally or in part therefrom, including suture coatings, are also described.

25 Claims, 1 Drawing Sheet

BIOABSORBABLE COMPOSITION AND COATINGS INCLUDING SAME

REFERENCE TO RELATED APPLICATIONS

This application claims the benefit of and priority to International Patent Application No. PCT/US2004/001759, filed Jan. 23, 2004, which claims the benefit of and priority to . U.S. Provisional Patent Application Ser. No. 60/442,730, filed Jan. 24, 2003, the entire disclosures of each of which are incorporated herein by this reference.

TECHNICAL FIELD

Bioabsorbable compositions of A) blends of bioabsorbable homopolymers and/or copolymers containing glycolide and lactide and B) salts of fatty acids and fatty acid esters are described. Processes for making the compositions and surgical articles made totally or in part therefrom, including suture coatings, are also described.

BACKROUND

Synthetic absorbable multifilament sutures such as Dexon, Polysorb, and Vicryl, commercially available from United States Surgical, a division of Tyco Healthcare Group, L. P. (Norwalk, Conn.), hereinafter USS, and Ethicon, Inc. (Somerville, N.J.), respectively, are well known in the industry.

Surgical suture coatings are known in the art. An important feature of a suture coating is its ability to enhance the suture's handling characteristics suture, such as the ease of a sliding a knot into place on the suture (referred to as knot repositioning or knot run down) without being so lubricious as to sacrifice knot security.

Suture coatings for synthetic absorbable sutures containing caprolactone are well known, see for example U.S. Pat. Nos. 4,624,256; 4,190,720; 4,582,052; 4,605,730; 4,700,704; 4,705,820; 4,788,979; 4,791,929; 4,994,074; 5,047,048; 5,100,433; 5,133,739; 5,352,515. Suture coatings containing esters of fatty acids are also known see for example U.S. Pat. Nos. 5,032,638, 4,711,241, 4,705,820, and 4,027,676.

In the early 1970's Ethicon introduced uncoated Vicryl; see for example Horton C. E., Adamson J. E., Mladick R. A., et al: "Vicryl Synthetic Absorbable Sutures"; Am Surg, December 1974, pp 72930-31. However, this uncoated braided multifilament caused tissue trauma (tissue drag) and handling problems. As a result, in the late 1970's a Vicryl suture coated with a glycolide/lactide copolymer blended with calcium stearate was introduced; see for example Saunder's R. A. et al: "Coated Vicryl Suture in Extraocular Muscle Surgery". Ophthalmic Surg 10: 13-8, July 1979 and Kobayashi H et al "Coated Polyglactin 910—a New Synthetic Absorbable Suture". Jpn J Surg 11 (6):467-75, November 1981. U.S. Pat. No. 4,201,216 discloses a glycolide/lactide copolymer blended with calcium stearate as a suture coating.

Then U.S. Pat. No. 5,716,376 provided a surgical suture coating comprising a) a copolymer comprising a predominant amount of epsilon-caprolactone and a minor amount of at least one other copolymerizable monomer and b) a salt of a lactylate ester of a $C_{10}$ or greater fatty acid selected from the group consisting of calcium stearoyl lactylate, magnesium stearoyl lactylate, aluminum stearoyl lactylate, barium stearoyl lactylate, zinc stearoyl lactylate, calcium palmityl lactylate, magnesium palmityl lactylate, aluminum palmityl lactylate, barium palmityl lactylate, or zinc palmityl lactylate, calcium olelyl lactylate, magnesium olelyl lactylate, aluminum olelyl lactylate, barium olelyl lactylate, and zinc olelyl lactylate.

U.S. Pat. No. 5,312,437 discloses an absorbable suture coating composition comprising the product obtained by reacting a mixture of poly(oxypropylene)glycol and a coplymer of lactide/glycolide copolymer.

U.S. Pat. No. 5,425,949 discloses a bioabsorbable copolymer obtained by polymerizing a major amount of epsilon-caprolactone and a minor amount of at least one other copolymerizable monomer in the presence of a polyhydric alcohol initiator. The copolymer can be used as a suture coating.

U.S. Pat. No. 6,177,094 discloses a bioabsorbable blend comprising the reaction product of component A and component B wherein component A comprises a copolymer obtained by polymerizing a major amount of epsilon-caprolactone and a minor amount of at least one other copolymerizable monomer in the presence of polyhydric alcohol as initiator; and component B comprises a composition comprising the product obtained by reacting a mixture of poly (propylene)glycol and lactide glycolide copolymer. The blend can be used as a suture coating.

Although commercially available surgical sutures such as Polysorb have excellent handling characteristics, it would be advantageous to provide another bioabsorbable suture coating that even further enhances the physical characteristics of the surgical sutures that it coats.

SUMMARY

A composition useful for coating surgical sutures has been found. The composition comprises 1) a blend of bioabsorbable polymer or copolymer, preferably a glycolide/lactide copolymer, and the reaction product of a bioabsorbable copolymer obtained by polymerizing a major amount of epsilon-caprolactone and a minor amount of at least one other copolymerizable monomer, optionally in the presence of a polyhydric alcohol initiator, and 2) a fatty acid salt, preferably calcium stearate or a salt of a fatty acid ester, preferably calcium stearoyl lactylate.

DESCRIPTION OF THE PREFERED EMBODIMENTS

Figure 1:
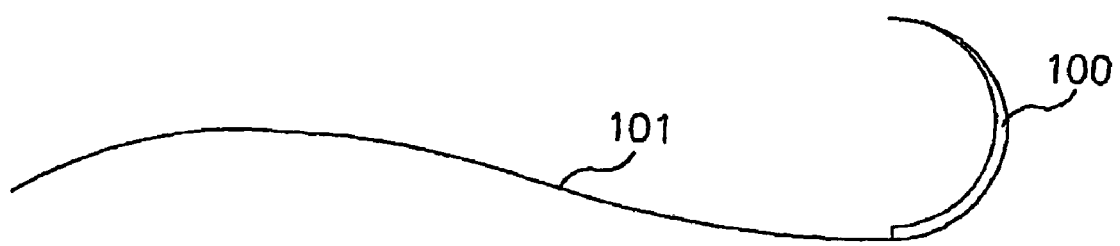
FIG. 1 is a perspective view of a coated suture attached to a needle described herein

The bioabsorbable blend may be prepared by conventional methods well known in the art. Preferably, about 10 to about 90 percent by weight epsilon-caprolactone containing copolymer is mixed with about 90 to about 10 percent by weight of bioabsorbable polymer and/or copolymer at about ambient temperature and stirred for about 4 hours. More preferably, about 40 to 60 percent by weight epsilon-caprolactone containing copolymer is mixed with about 60 to 40 percent by weight a bioabsorbable polymer and/or copolymer at ambient temperature and stirred for about 4 hours. Most preferably about 50 percent by weight epsilon-caprolactone containing copolymer is mixed with about 50 percent by weight of bioabsorbable copolymer at ambient temperature and stirred for about 4 hours. In an embodiment, the epsilon caprolactone containing copolymer is mixed with the bioabsorbable copolymer and then dissolved in a solvent cocktail to which the fatty acid salt or fatty acid ester salt is added with stirring for at least about an hour.

The ratio of the blend polymer and the fatty acid salt or the fatty acid ester salt in the coating composition may vary depending upon the specific components selected and the particular suture being coated. The ratio of polymer to salt is suitably within the range of 4:1 to 1:4 parts by weight and preferably is about 1:1 parts by weight.

Preferably the solvent contains methylene chloride, ethanol, and acetone. Most preferably the solvent composition is fabricated such that the density of the polymer solution matches that of the salt, while maintaining the solubility of the polymer blend. Suitable solvent compositions include about 60 to about 65 percent by weight methylene chloride, about 18 to about 0 percent by weight ethanol, and about 22 to about 35 percent by weight acetone.

Suitable caprolactone containing copolymers include copolymers which may be synthesized by well known conventional polymerization techniques; see, for example Principles of polymerization, George Odian, III Edition; 1991 pp. 569-573, the contents of which are incorporated herein by reference.

In one embodiment, the caprolactone containing copolymer is obtained by polymerizing a major amount of epsilon-caprolactone and a minor amount of at least one other copolymerizable monomer or mixture of such monomers. In another embodiment, the polymerization of the above occurs in the presence of a polyhydric alcohol initiator. The polymerization of these monomers contemplates all of the various types of monomer addition, i.e., simultaneous, sequential, simultaneous followed by sequential sequential followed by simultaneous, etc.

The copolymer herein can contain from about 70 to about 98, and preferably from about 80 to about 95, weight percent epsilon-caprolactone derived units, the balance of the copolymer being derived from the other copolymerizable monomer (s).

Suitable monomers which can be copolymerized with epsilon-caprolactone include alkylene carbonates such as trimethylene carbonate, tetramethylenecarbonate, dimethyl trimethylene carbonate; dioxanones; dioxepanones; absorbable cyclic amides; absorbable cyclic ether-esters derived from crown ethers; hydroxyacids capable of esterification, including both alpha hydroxy acids (such as glycolic acid and lactic acid) and beta hydroxyacids (such as beta hydroxybutyric acid and gamma hydroxyvaleric acid); polyalkyl ethers (such as polyethylene glycol and polyloropyline glycol and combinations thereof; with glycolide being a preferred monomer.

Suitable polyhydric alcohol initiators include glycerol, trimethylolpropane, 1,2,4-butanetriol, 1,2,6-hexanetriol, triethanolamine, triisopropanolamine, erythritol, threitol, pentaerythritol, ribitol arabinitol, xylitol, N,N,N',N'-tetrakis(2-hydroxyethyl)ethylenediamine, N,N,N',N'-tetrakis(2-hydroxypropyl)ethylenediamine, dipentaerythritol, allitol, dulcitol, glucitol, altritol, iditol, sorbitol, mannitol, inositol, and the like; with mannitol being preferred.

The polyhydric alcohol initiator is generally employed in small amounts, e.g., from about 0.01 to about 5, and preferably from about 0.1 to about 3, weight percent of the total monomer mixture.

Suitable bioabsorbable polymers include homopolymers of lactide and glycolide, as well as, copolymers of lactide or glycolide and poly (p-dioxanone), poly(alkylene oxalate), copolymers of vinyl acetates with unsaturated carboxylic acids such as crotonic, acrylic, and methacrylic acids; water soluble or dispersible cellulose derivatives such as methyl cellulose, hydroxymethyl cellulose and carboxymethyl cellulose; natural gums; ethylene oxide polymers; polyacrylamide; collagen; gelatin; polyamino acids; polyvinyl alcohol; polyvinyl pyrrolidone; absorbable conjugated unsaturated triglycerides such as dehydrated castor oil, and mixtures thereof. Glycolide/lactide copolymers are preferred. Copolymers containing about 15 to about 85 mole percent lactide are more preferred. Copolymers contain about 65 lactide mole percent and 35 mole percent glycolide are most preferred.

Suitable fatty acid salts include the calcium, magnesium, barium, aluminum, and zinc salts of $C_6$ and higher fatty acids, particularly those having from about 12 to 22 carbon atoms and mixtures thereof. The calcium salts of stearic, palmitic and oleic acids are preferred.

Suitable fatty acid ester salts include a lactylate ester of a $C_{10}$ or greater fatty acid, such as magnesium stearoyl lactylate, aluminum stearoyl lactylate, barium stearoyl lactylate zinc stearoyl lactylate, calcium palmityl lactylate, magnesium palmityl lactylate, aluminum palmityl lactylate barium palmityl lactylate, or zinc palmityl lactylate, calcium olelyl lactylate, magnesium olelyl lactylate, aluminum olelyl lactylate, barium olelyl lactylate, zinc olelyl lactylate or calcium stearoyl lactylate.

One or more medico-surgically useful substances may be incorporated into the composition, e.g., those which accelerate or beneficially modify the healing process when particles are applied to a surgical repair site. So, for example, the composition can carry a therapeutic agent which will be deposited at the repair site. The therapeutic agent can be chosen for its antimicrobial properties, capability for promoting repair or reconstruction and/or new tissue growth. Antimicrobial agents such as broad spectrum antibiotics (gentamycin, erythromycin or derivatized glycopeptides) which are slowly released into the tissue can be applied in this manner to aid in combating clinical and sub-clinical infections in a tissue repair site. Additional suitable antimicrobial agents include, β-lactams, quinolones, aminoglycosides, antibiotics (such as cephalosporins, penecillins, quinolones, tetracyclines, erythromycins, extended-spectrum macrolides, aminoglycosides, sulfonamides, chloramaphenicol clindamycin, vancomycin, spectinomycin, carbapenerns, monobactams, streptogramin, fosfomycin, tromethamines and teicoplanins) fusidic acid, novobiocin, minocycline, rifampin, and polymyxin. Also suitable are biocides such as heavy metals (Ag, Zn, Cu, Ge) their salts and derivatives; biguanides (such as chlorhexidine, alexidine, and polymeric biguanides), their salts and derivatives; phenols and bisphenols (such as triclosan and hexachlorophene) their salts and derivatives; halogen releasing agents (such as iodine and iodosphers); and quatenary ammonium compounds. The composition may also include antiseptics, anesthetics and anti-inflammatory agents. To promote repair and/or tissue growth, one or several growth promoting factors can be introduced into the sutures, e.g., fibroblast growth factor, bone growth factor, epidermal growth factor, platelet derived growth factor, macrophage derived growth factor, alveolar derived growth factor, monocyte derived growth factor, magainin, and so forth. Some therapeutic indications are: glycerol with tissue or kidney plasminogen activator to cause thrombosis, superoxide dimutase to scavenge tissue damaging free radicals, tumor necrosis factor for cancer therapy or colony stimulating factor and interferon, interleukin-2 or other lymphokine to enhance the immune system.

It is contemplated that composition may be dyed to increase visibility if used in the surgical field. Dyes known to be suitable for incorporation in sutures can be used. Such dyes include but are not limited to carbon black, bone black, D&C Green No. 6, and D&C Violet No. 2 as described in the handbook of U.S. Colorants for Food, Drugs and Cosmetics by Daniel M. Marrion (1979).

While the composition herein can be applied to any type of suture, it is essentially intended for application to a braided suture, a preferred type of which is disclosed in U.S. Pat. No. 5,019,093. The amount of composition applied to a braided suture will vary depending upon the structure of the suture, e.g., the number of filaments, tightness of braid or twist, the size of the suture and its composition. Suitable coating levels range from about 0.3% to about 15% with about 0.5% to about 8% being preferred.

The coated suture, suture 101, may be attached to a surgical needle 100 as shown in FIG. 1 by methods well known in the art. Wounds may be sutured by passing the needled suture through tissue to create wound closure. The needle preferably is then removed from the suture and the suture tied.

The following examples are given as an illustration of the preparation of copolymers, blends and coatings described herein as well as of the preparation and superior characteristics of the sutures described herein. It should be noted that the invention is not limited to the specific details embodied in the examples.

EXAMPLES

Example 1

Dry glycolide (200 grams), epsilon-caprolactone (1800 grams), stannous octoate as catalyst (0.40 grams) and dry d. mannitol as initiator (3.0 grams) were mixed under nitrogen for one hour. The mixture was heated in a reactor at a temperature of 160° C. for 12 hours. The epsilon-caprolactonel-glycolide copolymer was then sampled.

Example 2

Dry glycolide (610 g), L-Lactide (1390 g), stannous octoate as catalyst (0.40 g), and dry dodecanol as initiator (2.60 g) were mixed under N2 in a reactor for 1 hour. The mixture was heated in a reactor at a 160° C. for 8 hours. The 1-lactide/glycolide copolymer was then sampled.

Example 3

In a 500 mL container, 176.7 grams methylene chloride, 39.9 grams ethanol, and 68.4 grams acetone were mixed for 15 minutes at ambient conditions. To the above solution, 3.75 g of the copolymer of Example 2 and 3.75 grams of the copolymer of Example 1 were added while the solution was being stirred. The stirring was continued for 3 hours or until all the copolymers were completely dissolved. 7.5 grams of calcium stearate were added while the solution was stirred. The stirring continued for at about an hour to ensure complete dispersion of the salt.

Example 4

A size 2/0 Polysorb surgical suture was drawn through a coating solution applicator which applied the coating solution of Example 3, at a level of about 2.1 percent by weight of the suture, to coat the suture with the coating solution.

Example 5

A size 2/0 Polysorb surgical suture was drawn through a coating solution applicator which applied the coating solution of Example 3, at a level of about 2.8 percent by weight of the suture, to coat the suture with the coating solution.

Example 6

A size 2/0 Polysorb surgical suture was drawn through a coating solution applicator which applied the coating solution of Example 3, at a level of about 3.5 percent by weight of the suture, to coat the suture with the coating solution.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended hereto.

What is claimed is:

1. A bioabsorbable composition comprising:
   1) a blend of component A and B;
   2) salt of a fatty acid; and
   one or more medico-surgically useful substances;
   wherein component A comprises the reaction product of a bioabsorbable copolymer obtained by polymerizing a major amount of epsilon-caprolactone and a minor amount of at least one other copolymerizable monomer and component B comprises a member selected from the group consisting of bioabsorbable polymer and bioabsorbable copolymer.

2. The composition of claim 1 wherein the fatty acid salts are selected from the group consisting of the magnesium, barium, aluminum, and zinc salts of $C_6$ and higher fatty acids and mixtures thereof.

3. The composition of claim 1 wherein the fatty acid salts are selected from the group consisting of the magnesium, barium, aluminum, and zinc salts of about $C_{12}$ to about $C_{22}$ fatty acids and mixtures thereof.

4. The composition of claim 1 wherein the fatty acid salts are selected from the group consisting of the calcium of about $C_{12}$ to about $C_{22}$ fatty acids and mixtures thereof.

5. The composition of claim 1 wherein the fatty acid salts are calcium salts of stearic, palmitic and oleic acids.

6. The composition of claim 1 wherein the fatty acid salt is calcium stearate.

7. The composition of claim 1 wherein component A comprises the reaction product of a bioabsorbable copolymer obtained by polymerizing a major amount of epsilon-caprolactone and a minor amount of at least one other copolymerizable monomer in the presence of a polyhydric alcohol initiator.

8. The composition of claim 7 wherein the polyhydric alcohol initiator is selected from the group consisting of glycerol, trimethylolpropane, 1,2,4-butanetriol, 1,2,6-hexanetriol, triethanolamine, triisopropanolamine, erythritol, threitol, pentaerythritol, ribitol, arabinitol, xylitol, N,N,N',N'-tetraois(2-hydroxy-ethyl)ethylenediamine, N,N,N',N'-tetraois(2-hydroxypropyl)ethylenediamine, dipentaerythritol, allitol, dulcitol, glucitol, altritol, iditol, sorbitol, mannitol and inositol.

9. The composition of claim 1 wherein the other copolymerizable monomer is selected from the group consisting of glycolide, lactide, p-dioxanone and trimethylene carbonate.

10. The composition of claim 1 wherein the copolymer of component A comprises from about 70 to about 98 weight percent epsilon-caprolactone-derived units, the balance of the copolymer being derived from the other copolymerizable monomer(s).

11. The composition of claim 1 wherein the copolymer of component A comprises from about 80 to about 95 weight percent epsilon-caprolactone derived units, the balance of the copolymer being derived from the other copolymerizable monomer(s).

12. The composition of claim 2 wherein the polyhydric alcohol is employed in an amount from about 0.5 to about 5 weight percent of the total monomer mixture.

13. The composition of claim 1 wherein the polyhydric alcohol initiator is employed in an amount of from about 0.1 to about 2 weight percent of the total monomer mixture.

14. The composition of claim 1 wherein the bioabsorbable copolymer of component B is a copolymer of glycolide and lactide.

15. The composition of claim 14 wherein the copolymer of glycolide and lactide comprises from about 90 to about 65 mole percent lactide and from about 10 to about 35 mole percent glycolide.

16. The composition of claim 1 wherein the weight ratio of the salt of a fatty acid to blend of component A and component B is from about 4:1 to about 1:4.

17. The composition of claim 1 wherein the weight ratio of the salt of a fatty acid to blend of component A and component B is from about 1:1.

18. The composition of claim 1 wherein the blend comprises about 10 to about 90 weight percent of component A and 90 to about 10 weight percent of component B.

19. The composition of claim 1, comprising at least one member selected from the group consisting of antimicrobial agents, growth promoting agents, antiseptics, anesthetics and anti-inflammatory agents.

20. The composition of claim 19 wherein the antimicrobial agent comprises a member selected from the group consisting of glycopeptides, β-lactams, quinolones, aminoglycosides, antibiotics heavy metals, heavy metal salts, heavy metal derivatives, biguanides, biguanide salts, biguanide derivatives, phenol, bisphenols, phenol salts, bisphenol salts, phenol derivatives bisphenol derivatives, iodine, iodosphers quaternary ammonium compounds, and combinations thereof.

21. The composition of claim 20 wherein the antibiotic is selected from the group consisting of gentamychins, cephalosporins, penecillins, quinolones, tetracyclines, erythromycins, extended-spectrum macrolides, aminoglycosides, sulfonamides, chloramaphenicol, clindamycin, vancomycin, spectinomycin, carbapenems, monobactams, streptogramin, fosfomycin, tromethamines, teicoplanins, fusidic acid, novobiocin, minocycline, rifampin, polymyxin and combinations thereof.

22. The composition of claim 20 wherein the biguanide is selected from the group consisting of chlorhexidine and alexidine and the phenol and bisphenol is selected from the group consisting of triclosan and hexachlorophene.

23. The composition of claim 18 wherein the blend comprises about 40 to about 60 weight percent of component A and about 60 to 40 weight percent of component B.

24. The composition of claim 18 wherein the blend comprises about 50 weight percent of component A and about 50 weight percent of component B.

25. The composition of claim 1 wherein the bioabsorbable polymer of component B comprises an alpha hydroxy acid.

* * * * *